(12) United States Patent
Matsumoto et al.

(10) Patent No.: US 8,786,867 B2
(45) Date of Patent: Jul. 22, 2014

(54) INSPECTION DEVICE AND INSPECTION METHOD FOR BOILER FURNACE WATER WALL TUBES

(75) Inventors: Hirotoshi Matsumoto, Nagasaki (JP); Keiji Ida, Nagasaki (JP); Hideaki Murata, Nagasaki (JP); Kai Zhang, Takasago (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 595 days.

(21) Appl. No.: 13/129,503

(22) PCT Filed: Jul. 9, 2009

(86) PCT No.: PCT/JP2009/062843
§ 371 (c)(1),
(2), (4) Date: Jul. 25, 2011

(87) PCT Pub. No.: WO2010/058624
PCT Pub. Date: May 27, 2010

(65) Prior Publication Data
US 2011/0279828 A1     Nov. 17, 2011

(30) Foreign Application Priority Data
Nov. 20, 2008   (JP) ................ 2008-296531

(51) Int. Cl.
*G01B 11/24* (2006.01)
*G01B 11/14* (2006.01)
*G01N 21/00* (2006.01)
*G01N 21/86* (2006.01)

(52) U.S. Cl.
USPC ........... 356/630; 356/601; 356/608; 356/614; 356/237.1; 250/559.2; 250/559.22; 250/559.27

(58) Field of Classification Search
USPC ............. 356/601, 608, 614, 630, 237.1; 250/559.2, 559.22, 559.27
See application file for complete search history.

(56) References Cited

U.S. PATENT DOCUMENTS 5,139,412 A * 8/1992 Kychakoff et al. ............ 431/12

FOREIGN PATENT DOCUMENTS

| JP | 9-203616 A | 8/1997 |
| JP | 09-257714 A | 10/1997 |

(Continued)

OTHER PUBLICATIONS

Chinese Notice of Allowance dated Dec. 12, 2012 issued in corresponding Chinese Patent Application No. 200980146256 with English translation (4 pages).

(Continued)

*Primary Examiner* — Tarifur Chowdhury
*Assistant Examiner* — Sunghee Y Gray
(74) *Attorney, Agent, or Firm* — Westerman, Hattori, Daniels & Adrian, LLP

(57) ABSTRACT

An inspection device and an inspection method for boiler furnace water wall tubes. The inspection device includes a scanner including columns placed upright and fixed by magnets onto the surfaces of multiple water wall tubes extending in the up-down direction on the inner wall surfaces of the boiler furnace, a support frame fixed to the columns to support a displacement sensor producing laser light to be irradiated onto the surface of a water wall tube, and a moving mechanism for moving the displacement sensor in the axial direction of the water wall tube relative to the support frame. A signal processing unit calculates the amount of reduced wall thickness of the water wall tube from a difference between the cross-sectional surface shape of the water wall tube based on a signal from the displacement sensor and a reference shape without reduction in wall thickness.

9 Claims, 13 Drawing Sheets

(56) References Cited

FOREIGN PATENT DOCUMENTS

| JP | 10-096713 A | 4/1998 |
|----|----|----|
| JP | 10-197219 A | 7/1998 |
| JP | 10-281731 A | 10/1998 |
| JP | 2001-254904 A | 9/2001 |
| JP | 2005-098936 A | 4/2005 |
| JP | 2009-204604 A | 9/2009 |
| JP | 2009-281925 A | 12/2009 |

OTHER PUBLICATIONS

Taiwanese Notice of Allowance dated Jul. 24, 2012, issued in corresponding Taiwanese Patent Application No. 098125258 with partial translation (4 pages).
International Preliminary on Patentability (Form PCT/IB/373) of International Application No. PCT/JP2009/062843 date of issuance Jun. 21, 2011 with form PCT/ISA/237.
Taiwanese Office Action dated Jan. 16, 2012, issued in corresponding Taiwanese Patent Application No. 098125258.
International Search Report of PCT/JP2009/062843, mailing date Oct. 27, 2009.
Decision to grant a Patent dated Oct. 2, 20112, issued in corresponding Japanese Patent Application No. 2008-296531, with English translation (6 pages).
Mexican Notice of Allowance dated Jan. 29, 2014, issued in corresponding Mexican Patent Application No. MX/a/2011/005273 (p. 1).

\* cited by examiner

Outside of furnace (Ambient side)

Furnace side (Combustion gas side)

INSPECTION DEVICE AND INSPECTION METHOD FOR BOILER FURNACE WATER WALL TUBES

TECHNICAL FIELD

The present invention relates to an inspection device and an inspection method for boiler furnace water wall tubes, and particularly to an inspection device and an inspection method for measuring the surface geometry of a water wall tube arranged in a boiler furnace using a non-contact sensor to evaluate the degree of corrosion of the water wall tube based on the measured value.

BACKGROUND ART

Due to the recent serious environmental problem, land boilers for power generation are required to reduce NOx in flue gas, and measures are often taken from the viewpoint of combustion technology, such as two-stage combustion with relatively low cost.

However, two-stage combustion makes the combustion atmosphere in a boiler furnace more reducing, causing a problem of corrosion of boiler components such as water wall tubes. The problem with the boiler furnace water wall tubes today is sulfidation corrosion due to a reducing atmosphere. Since this corrosion causes damage over a wide range in the furnace, it requires a lot of time and labor to identify the corrosion.

As shown in a boiler schematic diagram of FIG. 1, a boiler furnace 1 is generally constructed of four water walls 3 and the inside is burned by a burner. Inside the water walls 3, multiple water wall tubes 4 extend in the up-down direction (vertical direction) and are arranged adjacent to each other by welding or in contact with each other. Alternatively, the water walls 3 themselves may be made up of the multiple water wall tubes 4 extending in the up-down direction (vertical direction) and welded adjacent to each other. Then, water is poured into the water wall tubes 4 and heated therein to produce steam. Such a boiler furnace 1 is, for example, 70 m high, and the width of its side wall is about 30 m, with more than 100 water wall tubes 4 installed on one side wall face.

Therefore, in order to identify a location where damage from sulfidation corrosion is developing, visual inspection (to check for surface unevenness visually), palpation (to detect surface unevenness with bare hands), and further an ultrasonic thickness gauge are used. However, since the area to be inspected is large, it takes time and labor to inspect the area. Further, visual inspection is affected by the inspector's subjective view, and there is a problem that the results vary widely.

The ultrasonic thickness measurement is quantitatively reliable, but since it is a point measurement to measure wall thickness at a fixed point, it is not suitable for measuring general corrosion conditions of water wall tubes.

On the other hand, Patent Document 1 (Japanese Patent Application Laid-Open No. 09-257714) teaches an inspection device for inspecting surface abrasion conditions of water wall tubes in a boiler furnace.

In Patent Document 1, as shown in FIG. 15, a heat transfer tube group placed horizontally in the boiler is made up of a heat transfer tube bank 02 and a heat transfer tube cavity portion 03, where an inspection device 04 is placed between the heat transfer tube bank 02 and the heat transfer tube cavity portion 03. The inspection device 04 includes a machine body 05, a flexible arm 06 provided on the machine body 05 to be inserted into the heat transfer tube bank 02, an end fixture 07 attached to the tip of the flexible arm 06, and an inspection unit 09 including an optical detection sensor movable in the up-down direction along a guide mechanism 08 provided in the flexible arm 06.

In the case of inspecting the outer surfaces of heat transfer tubes 010, the flexible arm 06 is inserted into the heat transfer tube bank 02, and when it reaches the bottom of the heat transfer tube bank 02, the end fixture 07 at the tip of the flexible arm 06 is actuated to fix the tip end. Then, a heat transfer tube alignment mechanism 011 provided in the flexible arm 06 is inflated pneumatically or mechanically to push the heat transfer tubes 010 to spread out laterally in order to correct misalignment of heat transfer tube arrays. After that, the inspection unit 09 is moved up and down along the flexible arm 06 to carry out inspection during the vertical movement.

However, the inspection device shown in Patent Document 1 is an inspection device for the heat transfer tubes 010 in the boiler furnace constructed of the heat transfer tube bank 02 and the heat transfer tube cavity portion 03 when heat transfer tube groups are placed horizontally in the boiler, and it cannot be applied to a structure where water wall tubes are arranged adjacent to each other in a longitudinal direction (vertical direction) along boiler inner wall surfaces.

Further, Patent Document 1 only teaches that the inspection unit 09 can measure the wall thicknesses of the heat transfer tubes 010 in a non-contact manner, and mention is made of neither a specific technique for calculating the wall thicknesses of the heat transfer tubes nor calculation of the amount of reduced wall thickness.

[Patent Document 1] Japanese Patent Application Laid-Open No. 9-257714

SUMMARY OF THE INVENTION

In view of such a conventional technical problem, it is an object of the present invention to provide an inspection device and an inspection method for boiler furnace water wall tubes, which can inspect reduced wall thickness conditions of multiple water wall tubes, extending in an up-down direction (vertical direction) along inner wall surfaces of a boiler furnace and arranged adjacent to each other, accurately and efficiently over a wide range based on surface shapes of the water wall tubes measured by a laser displacement sensor.

In order to solve such a problem, a first invention provides an inspection device for boiler furnace water wall tubes, which inspects reduced wall conditions of multiple water wall tubes extending in a vertical direction along inner wall surfaces of a boiler furnace and arranged adjacent to each other, characterized by comprising: a leg placed upright and fixed by a magnet onto the surface of a water wall tube; a support frame fixed to the leg to support a displacement sensor producing laser light to be irradiated onto the surface of the water wall tube; a moving mechanism for moving the displacement sensor in the axial direction of the water wall tube relative to the support frame; and reduced wall thickness evaluating means for measuring the surface shape of the water wall tube along a direction substantially perpendicular to the axial direction of the water wall tube based on a signal from the displacement sensor to calculate the amount of reduced wall thickness of the water wall tube from a difference between the measurement result of the surface shape and a reference shape without reduction in wall thickness in order to evaluate a reduced wall thickness condition.

According to this invention, there can be provided a scanner with a sensor head on which the displacement sensor is mounted, including the leg placed upright and fixed by the magnet onto the surface of the water wall tube, the support frame fixed to the leg to support the displacement sensor producing laser light to be irradiated onto the surface of the water wall tube, and the moving mechanism for moving the displacement sensor in the axial direction of the water wall tube relative to the support frame.

Since it is fixed by the magnet to the water wall tube on a furnace wall, the fixation can be ensured. Further, since movement to a position to be measured is easy, portions to be measured can be measured efficiently.

In addition, since the cross-sectional surface shape of the water wall tube is measured along the direction substantially perpendicular to the axial direction of the water wall tube based on the signal from the displacement sensor to calculate the amount of reduced wall thickness from the difference between the measurement result of the surface shape and the reference shape without reduction in wall thickness, the amount of reduced wall thickness of the water wall tube and further remaining tube wall thickness can be calculated to evaluate a corrosion condition of the water wall tube from the amount of reduced wall thickness and the remaining tube wall thickness, making efficient the maintenance and inspection of water wall tubes.

In the first invention, it is preferred that the support frame be supported by a plurality of legs and that the support frame include adjustment mechanisms attached to the legs movably in the upright direction of the legs and in a direction perpendicular to the upright direction to make the position of the displacement sensor adjustable relative to the water wall tube.

According to this structure, since the position of the displacement sensor relative to the water wall tube becomes adjustable in the upright direction of the legs and in the direction perpendicular to the upright direction by means of the adjustment mechanisms, the distance to the water wall tube is adjusted to keep it constant in order to minimize the inclination of the displacement sensor, so that error in measuring the cross-sectional shape of the water wall tube can be reduced, thereby improving measurement accuracy.

It is also preferred that the reduced wall thickness evaluating means include a reference position calculating section for calculating a reference position for superposition between the measurement result of the surface shape and the reference shape without reduction in wall thickness.

According to this structure, since the reference position calculating means calculates the reference position of the surface shape, and the measurement result of the surface shape and a design reference shape are superposed based on the reference position, the difference can be calculated accurately and hence the amount of reduced wall thickness can be calculated accurately.

It is further preferred that the reduced wall thickness evaluating means include a correction section for correcting the inclination and position of the surface shape based on the signal from the displacement sensor at the time of the superposition.

According to this structure, the surface shape obtained from the displacement sensor may be inclined or moved up or down as the measurement result depending on vibration of the laser displacement sensor and further on an inclination in the initial installed state. However, the reference position is calculated from the measurement result to correct an inclination in the circumferential direction and a up-down positional relationship of the water wall tube 4 in such a manner to match the reference position to a position corresponding to a reference position in the reference shape without reduction in wall thickness, so that superposition can be performed accurately, and hence measurement error can be reduced.

Further, even if the laser displacement sensor does not travel in parallel to the water wall tube due to lateral movement depending on the initial installed state, the lateral positional relationship of the water wall tube can be corrected in the same manner, so that superposition can be performed accurately and hence measurement error can be reduced. Further, since the measurement error can be reduced even if not being parallel, installation time can be reduced to a large extent.

Further, it is preferred that the reference position be a position of a membrane provided to protrude radially in order to connect adjacent water wall tubes. According to this structure, if the degree of corrosion in the membrane is lower than the circumferential portions of the water wall tube that face the inside of the boiler furnace, this position can be set as the reference position.

When the amount of reduced wall thickness of the water wall tube is slight, the error in calculating a difference obtained from the superposition between the measurement result and the reference shape without reduction in wall thickness is small and hence inspection error is small. However, as the amount of reduced wall thickness increases, the thickness of the membrane is reduced. Therefore, when the amount of reduced wall thickness becomes large, the wall thickness of the membrane needs to be measured to correct the surface position of the membrane as well.

If the water wall tube is not connected by the membrane, it is preferred that the reference position be a contact or closest position between adjacent water wall tubes. Since the degree of corrosion is lower in the contact position or a close position than the circumferential portions of the water wall tube that face the inside of the boiler furnace, this position can be set as the reference position.

Further, it is preferred that refraction means be provided between the displacement sensor producing laser light to be irradiated onto the surface of the water wall tube and the water wall tube to refract the laser light irradiated from the displacement sensor toward the water wall tube.

In general, a sensor head with the displacement sensor mounted thereon has a slit width and focal length fixed by its specifications. When inspection is performed at a scaffold level, a sensor head having a narrow slit width and a short focal length is used to meet the requirements while increasing the number of scans. However, according to the above-mentioned structure, since the laser light is refracted toward the water wall tube, one tube can be scanned with the laser light even when the laser light is irradiated onto the water wall tube spaced a short distance from the scaffold in the boiler furnace in which the scanner is placed, so that the number of scans is reduced, thereby improving the efficiency of inspection.

Next, a second invention provides an inspection method for boiler furnace water wall tubes, which inspects reduced wall conditions of water wall tubes extending in a vertical direction along inner wall surfaces of a boiler furnace and arranged adjacent to each other, characterized in that the surface shape of a water wall tube is measured along a direction substantially perpendicular to the axial direction of the water wall tube based on a signal from a displacement sensor for irradiating laser light onto the surface of the water wall tube, a measurement result of the surface shape and a reference shape without reduction in wall thickness are superposed to calculate a difference therebetween based on a reference position of the surface shape, and the amount of reduced wall thickness of the water wall tube is calculated from the difference to evaluate a reduced wall condition.

According to this invention, since the surface shape of the water wall tube is measured along the direction substantially perpendicular to the axial direction of the water wall tube based on the signal from the displacement sensor, the measurement result of the surface shape and the reference shape without reduction in wall thickness are superposed to calculate the difference therebetween based on the reference position of the surface shape in order to calculate the amount of reduced wall thickness of the water wall tube, so that the amount of reduced wall thickness and further remaining tube wall thickness can be calculated to evaluate a corrosion condition of the water wall tube from the amount of reduced wall thickness and the remaining tube wall thickness, making efficient the maintenance and inspection of water wall tubes.

In the second invention, it is preferred that the inclination and position of the surface shape based on the signal from the displacement sensor be corrected and superposed at the time of the superposition.

In other words, the reference position is calculated from data on the measurement result to correct an inclination in the circumferential direction of the water wall tube and vertical and lateral positional relationships in such a manner to match the reference position to a position corresponding to a reference position without reduction in wall thickness, so that superposition can be performed accurately, and hence measurement error can be reduced.

In the second invention, it is also preferred that the remaining tube wall thickness be determined by subtracting the calculated amount of reduced wall thickness from a design wall thickness, and the remaining tube wall thickness be evaluated depending on whether the remaining tube wall thickness meets a design requiring wall thickness. According to this structure, it is determined, based on the preset design requiring wall thickness, whether the remaining tube wall thickness of the water wall tube falls in a dangerous range, enabling efficient maintenance and inspection.

According to the present invention, there can be provided an inspection device and an inspection method for boiler furnace water wall tubes, which can inspect reduced wall thickness conditions of multiple water wall tubes, extending in a vertical direction along inner wall surfaces of a boiler furnace and arranged adjacent to each other, accurately and efficiently over a wide range based on surface shapes of the water wall tubes measured by a laser displacement sensor.

MODE FOR CARRYING OUT THE INVENTION

Figure 1:
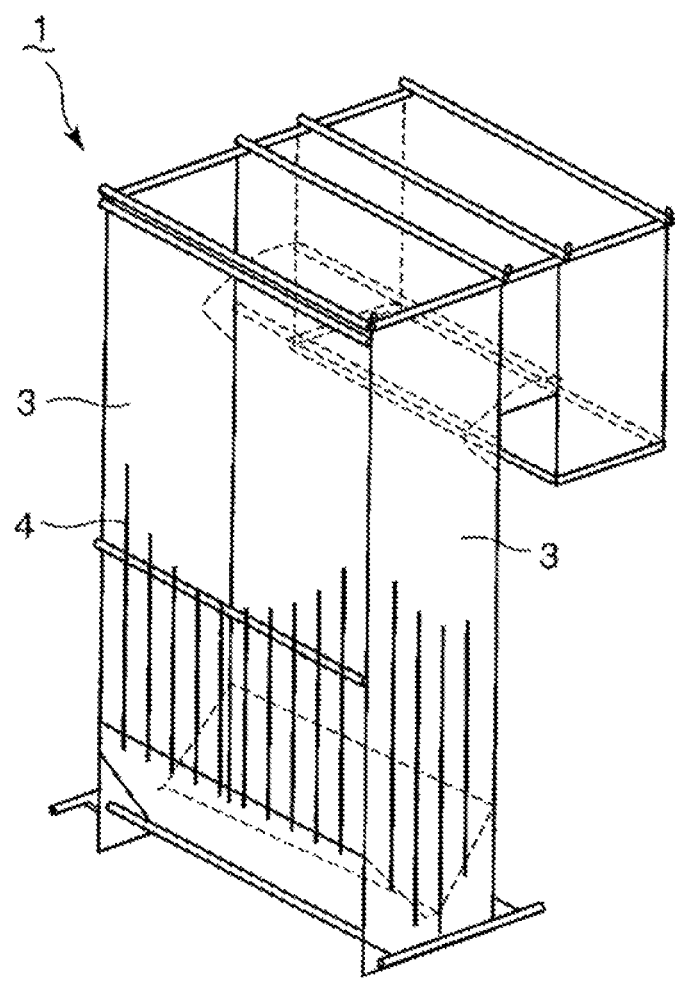
FIG. 1 It is a schematic diagram showing a boiler furnace.

The present invention will be described in detail below with reference to an embodiment shown in the drawings. Note that the size, material, shape, and relative position of components described in the embodiment do not limit the scope of this invention unless otherwise particularly mentioned, and the embodiment is just illustrative example.

A boiler schematic diagram is shown in FIG. 1. A boiler furnace 1 is constructed of four water walls 3 the inside of which is burned by a burner. Inside the water walls 3, multiple water wall tubes 4 extend in an up-down direction (vertical direction) and are arranged adjacent to each other by welding or in contact with each other. Alternatively, the water walls 3 themselves may be made up of the multiple water wall tubes 4 extending in the up-down direction (vertical direction) and welded adjacent to each other. Then, water is poured into the water wall tubes 4 and heated therein to produce steam. For the water wall tubes 4, there are two types: a smooth tube type whose tube passage is linear and a rifled tube type with a spiral groove formed in a linear tube passage.

Figure 2A:
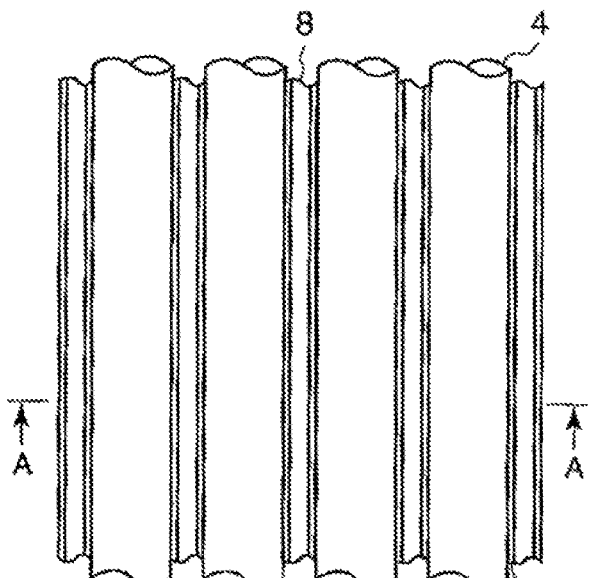
FIG. 2 It shows a detailed structure of water wall tubes in an aligned state, where (a) is an overall front view, and (b) is a cross-sectional view along line A-A.
Figure 2B:
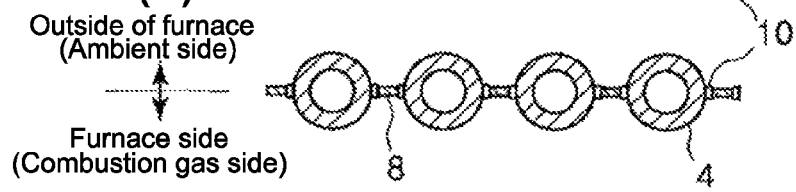
Figure 3A:
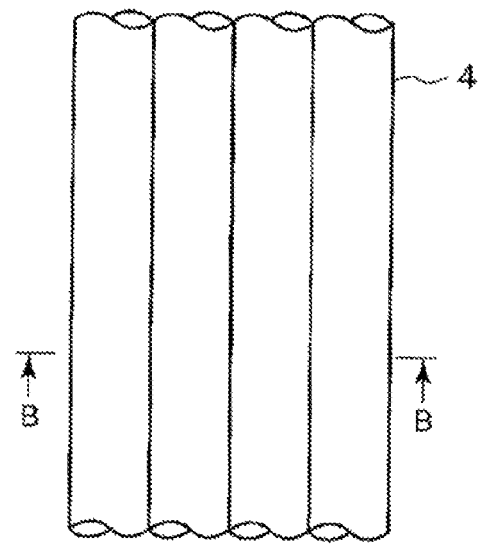
FIG. 3 It shows another detailed structure of water wall tubes in an aligned state, where (a) is an overall front view, and (b) is a cross-sectional view along line B-B.
Figure 3B:
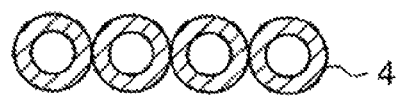

Detailed structures of the water wall tubes 4 are shown in FIG. 2 and FIG. 3. FIG. 2 shows a structure where the multiple water wall tubes 4 are jointed to adjacent ones through membranes 8, respectively. FIG. 2(b) shows a cross-sectional view along line A-A of FIG. 2(a).

The membrane 8 is a plate-like member extending in the axial direction of the water wall tubes 4, both ends of which are welded with a weld metal 10 to the water wall tubes 4 in diameter positions of the water wall tubes 4 to form the wall surface 3 of the boiler furnace 1 in such a state that the multiple water wall tubes 4 are aligned.

FIG. 3 is another example of the water wall tubes 4, where the multiple water wall tubes 4 are separate tubes up and down ends of which are fixed and each of which is arranged in contact with adjacent water wall tubes 4 in diametrically opposite positions along the inner wall of the wall surface 3 of the boiler furnace 1.

An inspection device 11 for inspecting the water wall tubes 4, structured as mentioned above, for reduced wall thickness conditions due to sulfidation corrosion in the furnace will be described.

This inspection device 11 consists of a scanner 14, which not only supports a laser displacement sensor 12 for measuring surface shapes of the water wall tubes 4 in a non-contact manner, but also moves the laser displacement sensor 12 in the axial direction of the water wall tubes 4, and a signal processing unit 16 for processing a measured signal from the laser displacement sensor 12 to calculate the amount of reduced wall thickness and remaining tube wall thickness in order to determine a corrosion condition.

Figure 4:
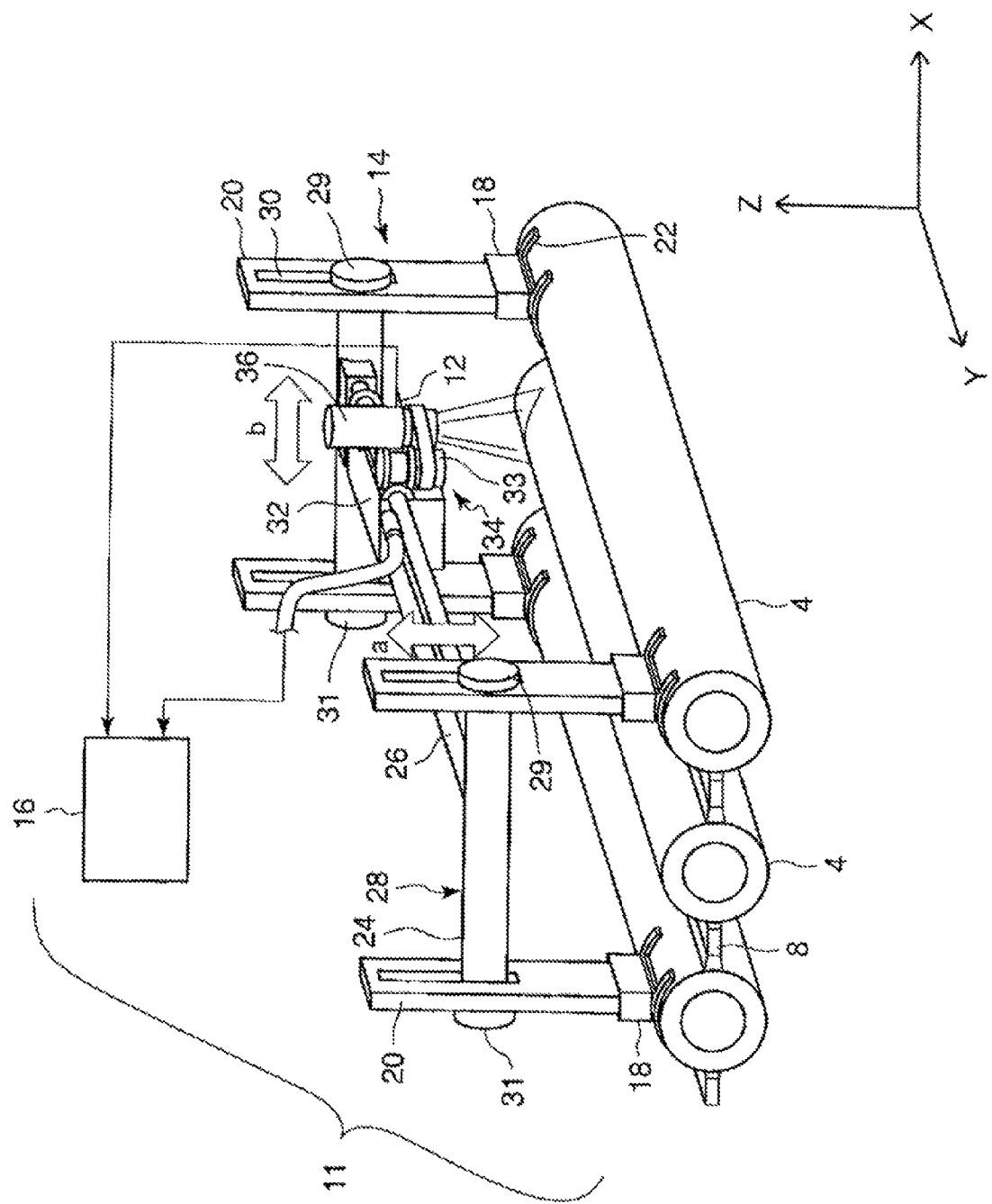
FIG. 4 It is a perspective view showing the general structure of the present invention.

As shown in FIG. 4, the scanner 14 is such that four columns (legs) 20 with light-weight magnets (magnets) 18 attached to their lower ends are placed upright and fixed. Seating faces 22 having an arc shape to fit the circular surfaces of the water wall tubes 4 are formed on surfaces of joint to the water wall tubes 4, respectively. The columns 20 are fixed at two positions in the axial direction of a water wall tube 4 and at two positions in the axial direction of another water wall tube 4 so that they will be positioned in corners of a rectangle.

Then, beams 24, 24 are provided in a hanging manner to connect the columns 20 on one water wall tube 4 with the columns 20 of the other water wall tube 4. Both ends of a rail 26 are attached to the beams 24, 24. The beams 24, 24 and the rail 26 form a support frame 28 for supporting the laser displacement sensor 12.

Further, the beam 24 is constructed with a screw mechanism so that the vertical positioning relative to the columns 20 is adjustable. Up-down adjusting knobs 29 are rotated to enable the beam to move in the Z-axis direction (direction of arrow a) in a region where a slit 30 is formed. The end of the rail 26 is also constructed to be movable relative to the beam 24 in the axial direction of the beam 24 by means of a screw mechanism. Lateral adjusting knobs 31 are rotated to enable movement in the X-axis direction (direction of arrow b).

A sensor head 32 is attached to the rail 26 in a manner to be movable in the Y-axis direction along the rail 26. Mounted on the sensor head 32 are a motor 33 for driving, an encoder 36 for outputting a traveling distance signal of the sensor head 32 from the rotation angle of the motor 33, and the laser displacement sensor 12 for irradiating laser light toward the surface of a water wall tube 4 to measure displacement. The motor 33 and the rail 26 constitute a moving mechanism 34 of the laser displacement sensor 12.

Figure 5A:
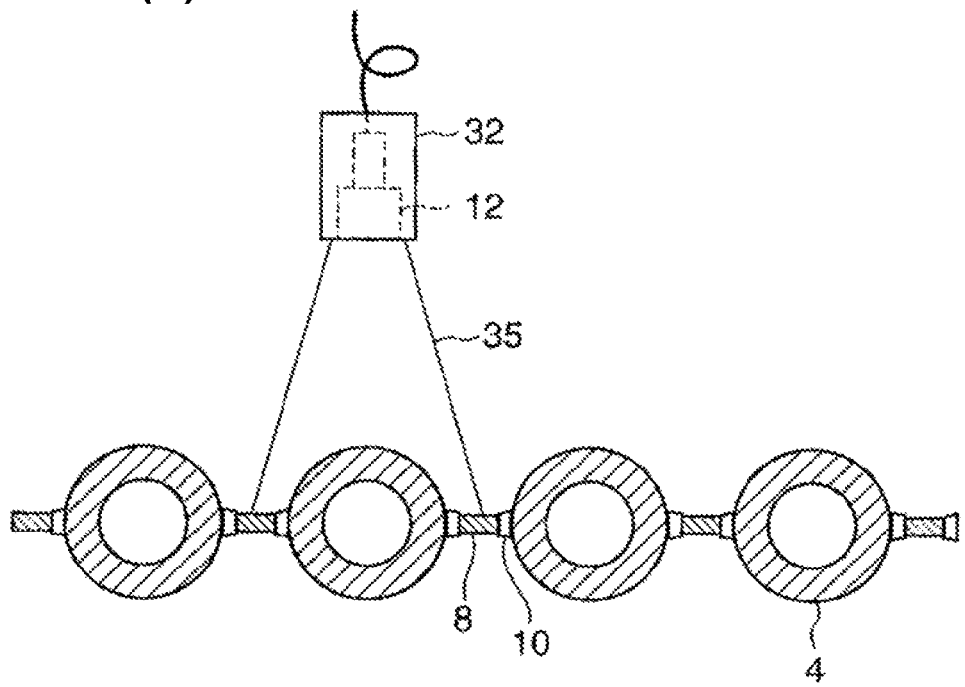
FIG. 5 It is an explanatory drawing showing irradiated states of a laser slit from a laser displacement sensor, where (a) indicates irradiation to water wall tubes connected by membranes, and (b) indicates irradiation in the case of separate tubes without being connected by membranes.

As shown in FIG. 5(a), (b), the laser displacement sensor 12 is a two-dimensional laser displacement sensor 12, which irradiates slit-like (band-shaped) laser light 35 in a direction substantially perpendicular to the longitudinal direction (axial direction) of a water wall tube 4 to measure reflected light in order to measure a distance to the water wall tube 4. The outer surface shape of the water wall tube 4 along a direction perpendicular to the axial direction of the water wall tube 4 is measured.

Figure 5B:
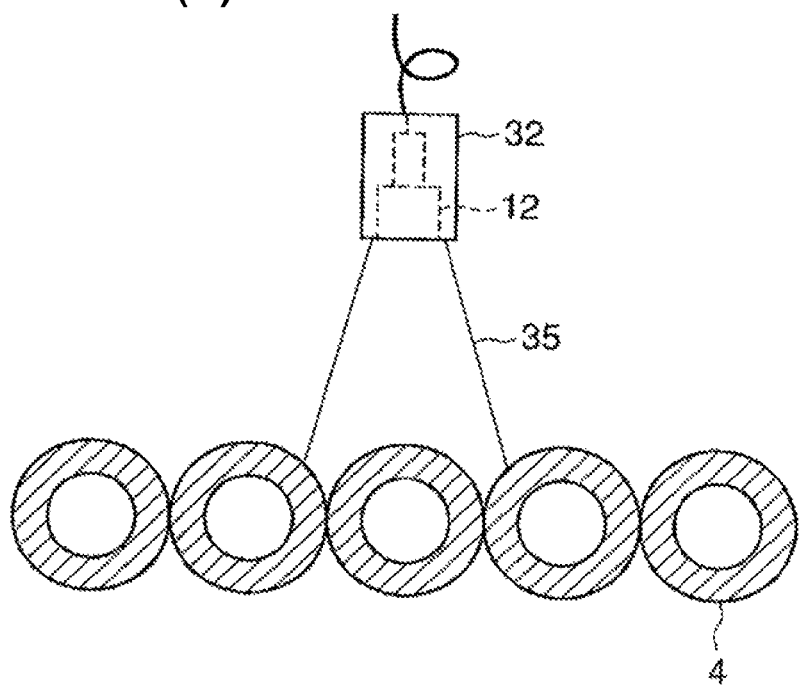

FIG. 5(a) shows an irradiated state of the laser slit when the water wall tubes 4 are connected by membranes 8. FIG. 5(b) shows an irradiated state of the laser slit when the water wall tubes 4 are separate tubes not connected with each other by membranes but arranged in contact with each other.

In the case of boiler furnace inspection, the inspection is carried out on a scaffold generally installed in the furnace. The clearance between the scaffold and the surface of a water wall tube 4 is about 150-300 mm. Therefore, when a location near the scaffold (scaffold level) is to be inspected, the focal length needs to be shortened. However, according to general specifications of the laser displacement sensor 12, as the focal length of laser light is shortened, since the slit width also becomes narrower, the surface of the water wall tube 4 may not be able to be covered by the slit laser light as shown in FIGS. 5(a), (b). In this case, the laser displacement sensor 12 needs to be moved toward the water wall tube 4 to measure the displacement of the surface of the water wall tube 4, resulting in reduction in the efficiency of inspection.

Figure 6A:
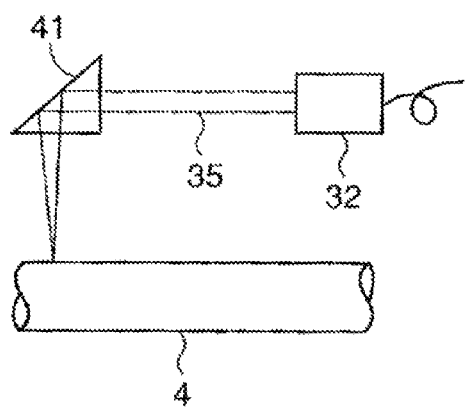
FIG. 6 It is an explanatory drawing showing irradiated states of the laser slit from the laser displacement sensor, where (a) indicates irradiation passing through a prism, and (b) indicates irradiation refracted by a mirror.

Therefore, as shown in FIGS. 6(a), (b), refraction means for refracting the laser light 35 is employed. As the refraction means, a prism 41 is provided in FIG. 6(a) so that the laser light 35 produced by the laser displacement sensor incorporated in the sensor head 32 will pass through the prism 41 to refract the laser light 35.

Figure 6B:
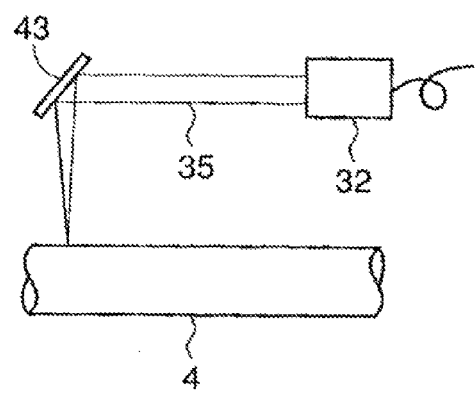

In FIG. 6(b), a mirror 43 is provided so that the laser light 35 produced by the laser displacement sensor will be refracted by the mirror 43.

Use of the refraction means shown in FIGS. 6(a), (b) enables scanning of one tube with laser even if a water wall tube whose distance to the scaffold is short is irradiated, so that the number of scans is reduced, thereby improving the efficiency of inspection.

The scanner 14 thus constructed is such that the four columns 20 are fixed by the light-weight magnets 18 in a highly corroded portion or a portion as a target for periodic check, and the sensor head 32 is mounted in an inspection region. After that, the up-down adjusting knobs 29 and the lateral adjusting knobs 31 are rotated to make adjustments so that the distance from the surface of a water wall tube 4 as the inspection target to the laser displacement sensor 12 will become constant.

Then, the laser displacement sensor 12 is scanned while irradiating laser light along the axial direction (longitudinal direction) of the water wall tube 4 by means of the motor 33 to measure surface shape data in a stroke range of the sensor head 32 (e.g., in a range of 300-500 mm). In this case, the encoder 36 can acquire the surface shape data at every fixed moving distance (e.g., 1-2 mm).

Since the scanner 14 is fixed onto the water wall tubes 4 by the magnets, the fixation can be ensured. Further, since movement to a position to be measured is easy, portions to be measured can be measured efficiently over a wide range.

Next, the signal processing unit 16 for processing a measurement signal from the laser displacement sensor 12 to calculate the amount of reduced wall thickness and remaining tube wall thickness in order to determine a corrosion condition will be described.

Figure 7:
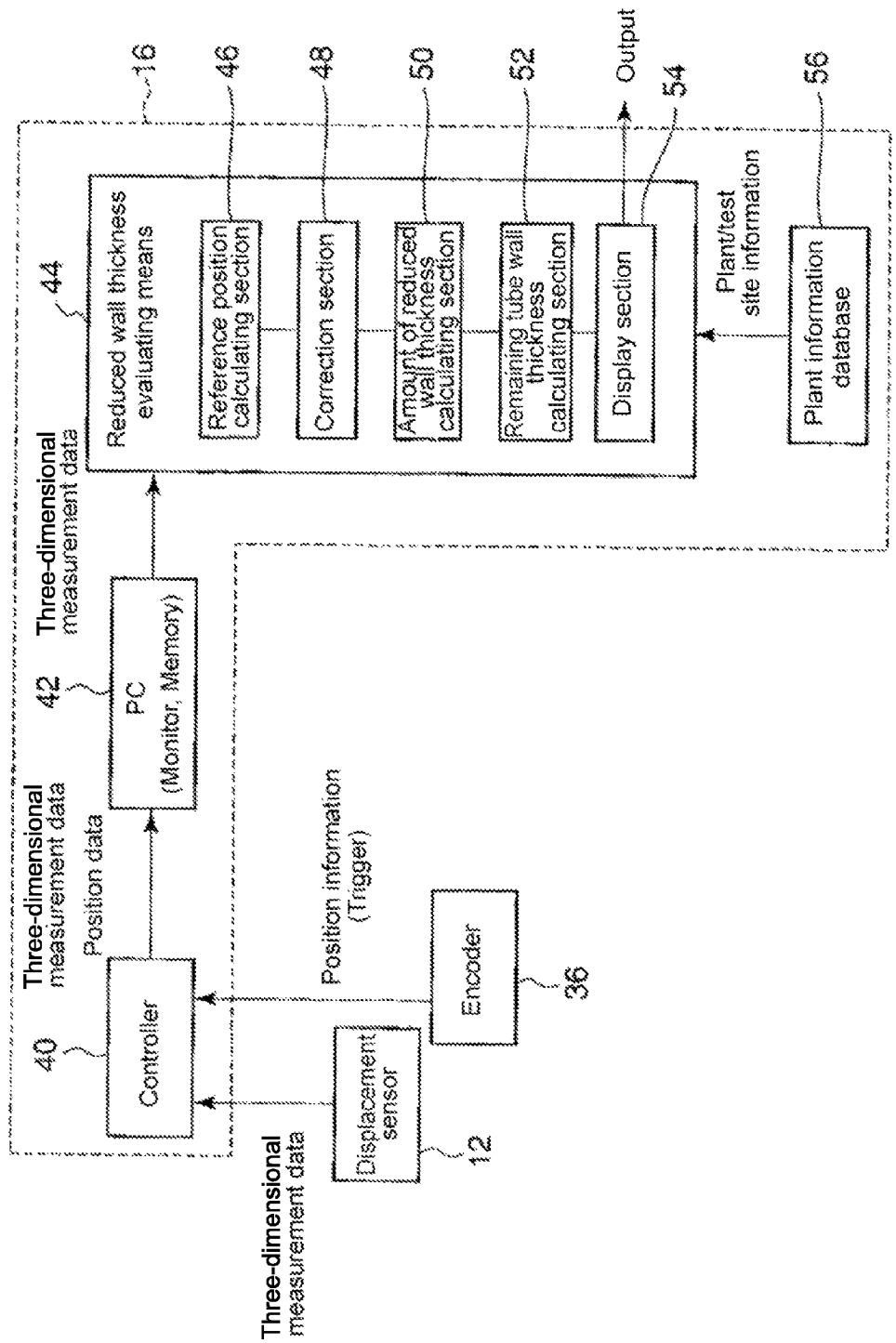
FIG. 7 It is a block diagram showing the general structure of a signal processing unit.

The general structure of this signal processing unit 16 is shown in FIG. 7. Displacement measurement data (three-dimensional measurement data) from the laser displacement sensor 12 and position information from the encoder 36 are input into a controller 40. The displacement measurement data (three-dimensional measurement data) is stored in a PC (computer of an inspection worker) 42 for every predetermined distance (e.g., 1-2 mm) together with distance information, and displayed on a screen.

The displacement measurement data (three-dimensional measurement data) stored in the PC 42 is input into reduced wall thickness evaluating means 44. This reduced wall thickness evaluating means 44 has a reference position calculating section 46 for calculating, from the displacement measurement data (three-dimensional measurement data), a reference position for calculating the amount of reduced wall thickness, a correction section 48 for correcting an inclination of the surface shape based on the displacement measurement data (three-dimensional measurement data) and vertical and lateral misalignment, an amount of reduced wall thickness calculating section 50 for superposing the surface shape from the displacement measurement data (three-dimensional measurement data) with a design reference shape to calculate the amount of reduced wall thickness from a difference as a result of the superposition, a remaining tube wall thickness calculating section 52 for calculating remaining tube wall thickness based on design data, and a display section 54 for evaluating the calculation results from the amount of reduced wall thickness calculating section 50 and the remaining tube wall thickness calculating section 52 and outputting the result on a display.

Plant/test site information is also input from a plant information database 56 into the reduced wall thickness evaluating means 44. For example, the name of a plant to be inspected, the name of a site to be tested, design data (design external diameter of the tube, design requiring thickness, material, etc.), past inspection history, similar plant data, etc. are input.

Figure 8:
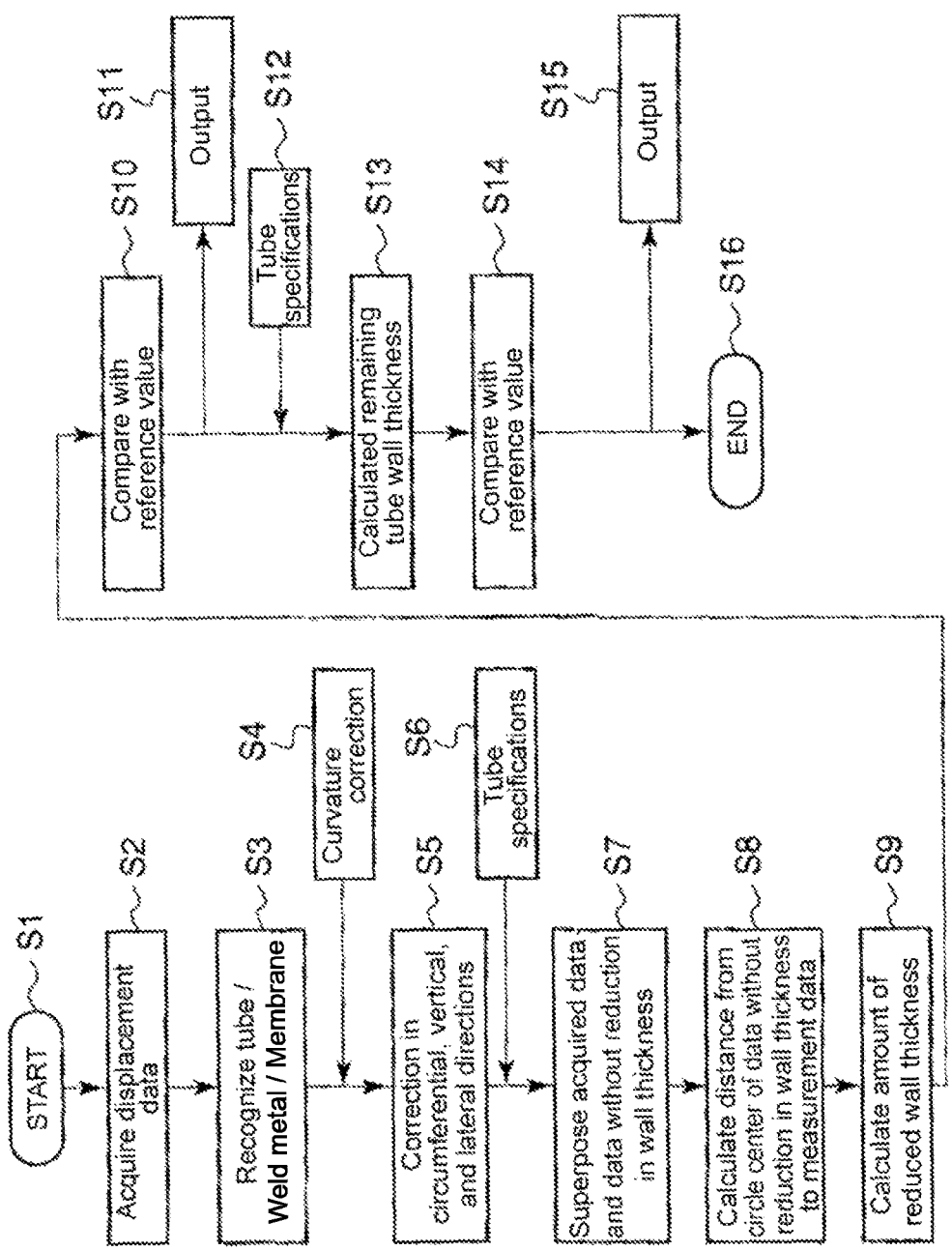
FIG. 8 It is a flowchart about an evaluation technique in reduced wall thickness evaluating means.

An evaluation technique in the reduced wall thickness evaluating means 44 will be described with reference to a flowchart of FIG. 8.

Figure 9:
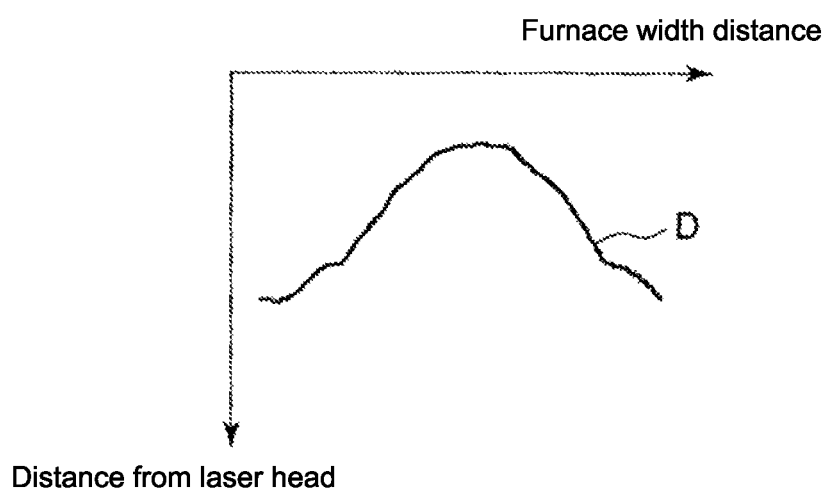
FIG. 9 It is an explanatory drawing of a surface shape through the laser displacement sensor.

First, when starting at step S1, displacement data associated with the position information is acquired in step S2. As the displacement data, as shown in FIG. 9, surface shape data D on the water wall tube 4 is acquired as displacement from the position of the sensor head 32, taking furnace width distance (distance in the X-axis direction shown in FIG. 4) on the abscissa.

Then, in step S3, a portion of the water wall tube 4, portions of the weld metal 10, and portions of the membranes 8 are recognized from the surface shape acquired by the reference position calculating section 46.

Figure 10B:
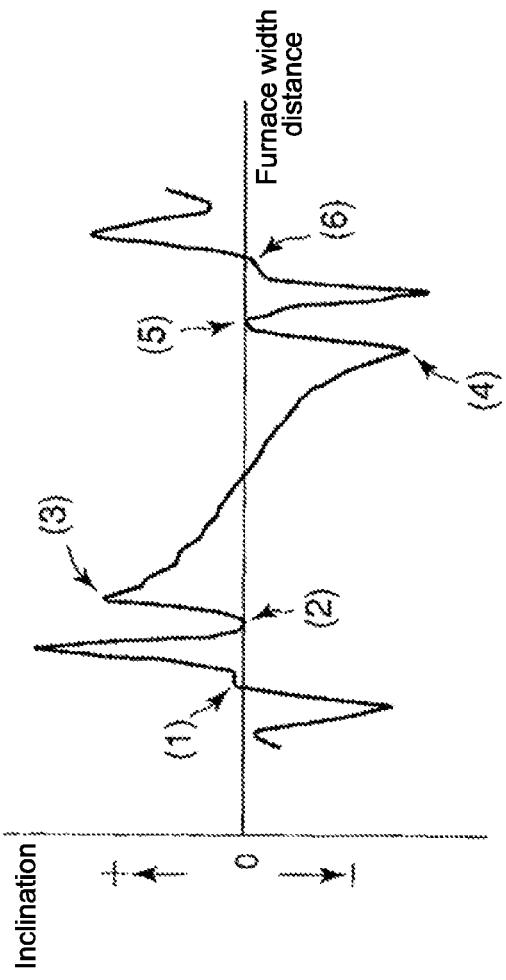
FIG. 10 It is an explanatory drawing showing, from the surface shape, a portion of a water wall tube, weld metal portions, and membrane portions, where (a) indicates a surface shape curve, and (b) indicates the characteristics of the first order derivative of the curve of (a).
Figure 10A:
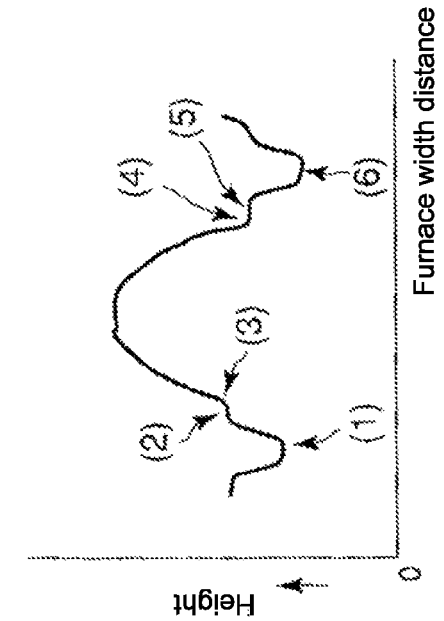

Specifically, as shown in FIG. 10(*a*), if the furnace width distance is taken on the abscissa and the height of the mountain-like surface shape on the ordinate, (1), (6) correspond to the portions of the membranes 8, (2), (5) correspond to the portions of the weld metal 10, and (3)-(4) correspond to the portion of the water wall tube 4.

These positions can be determined from the measurement data by calculating an inclination from the first order derivative of the curve of the mountain-like surface shape.

FIG. 10(*b*) shows the first order derivative data, where the inclination is almost zero in the portions (1), (6) of the membranes 8 and also in the portions (2), (5) because of weld metal pads.

Inclination peak values appear at two positions on the plus and minus sides, respectively. The position of the first peak value in the abscissa direction is in a transition from the membranes 8 to the weld metal 10, and the position (3) of the second peak value is in a transition from the weld metal to the water wall tube 4. Since this position (3) can be determined to be a boundary position P between the weld metal 10 and the water wall tube 4, it is found that (3)-(4) is the surface portion of the water wall tube 4.

Thus, the positions (1), (6) of the membranes 8, and the boundary positions (3), (4) are determined and used as reference positions for superposition during calculation of the amount of reduced wall thickness to be described later.

Further, the inclination is calculated from the first order differentiation of the curve of the mountain-like surface shape determined from the measurement data, and inflection points can be used to determine the positions of the membranes 8 and the boundary positions P (see FIG. 14) between the weld metals 10 and the water wall tube 4. Therefore, the reference positions are calculated reliably, improving the accuracy of calculation of the amount of reduced wall thickness.

Figure 11A:
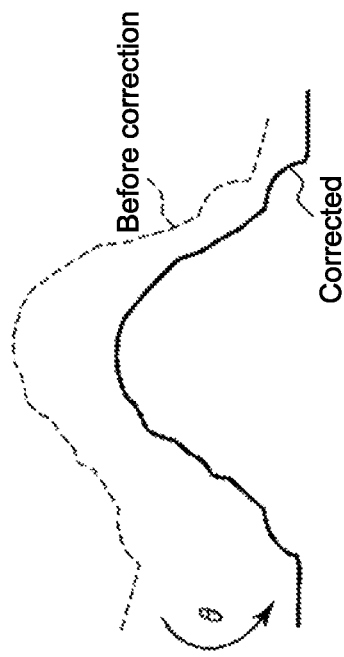
FIG. 11 It is an explanatory drawing showing corrected states of surface shape curves, where (a) indicates a correction in an up-down direction, and (b) indicates an inclination correction.
Figure 11B:
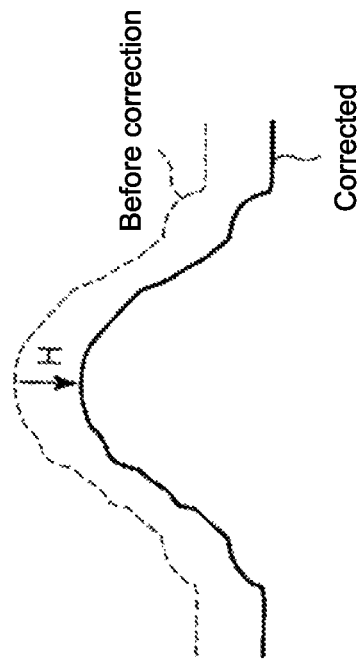
Figure 12:
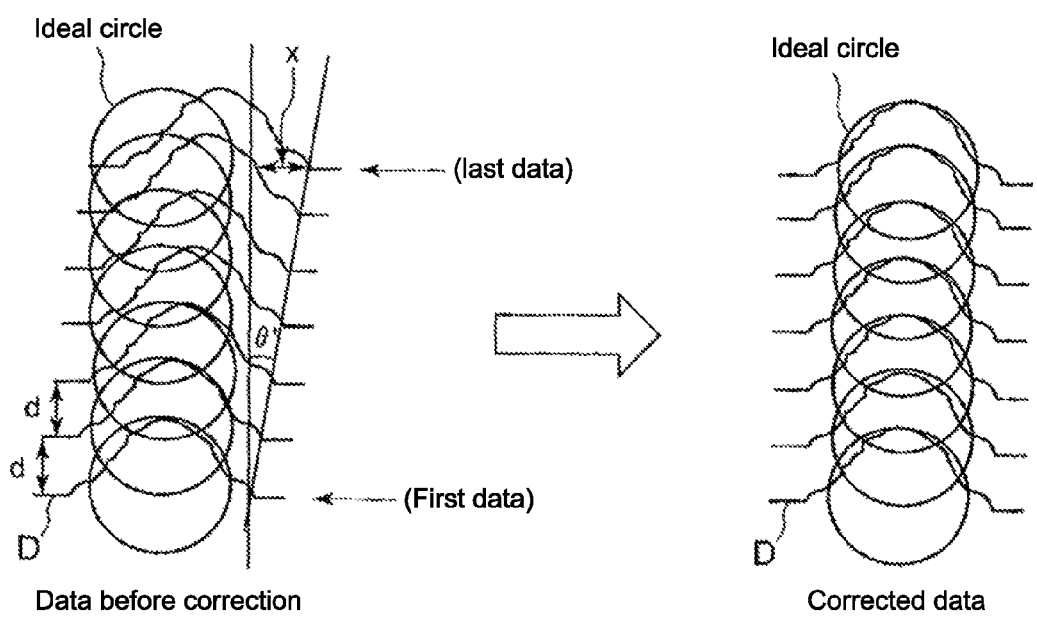
FIG. 12 It is an explanatory drawing showing a corrected state of surface shape curves in a lateral direction.

Next, curvature correction is made in step S4, and the procedure proceeds to step S5 in which, if the heights of the left and right positions (1) and (6) of the membranes 8 or the heights of the left and right boundary positions (3) and (4) in the surface shape determined from the measurement data do not match, the correction section 48 makes a correction to rotate the curve θ degrees in the circumferential direction of the water wall tube 4 as shown in FIG. 11(*b*) to match the heights horizontally.

If the positions (1), (6) of the membranes or the boundary positions (3), (4) determined from the measurement data are misaligned with membrane positions or boundary positions of a reference shape without reduction in wall thickness such as design data, the curve is moved distance H in the up-down direction as shown in FIG. 11(*a*). In FIGS. 11(*a*), (*b*), the doted line represents the shape position before correction and the solid line represents the corrected shape position.

Further, if the laser displacement sensor does not travel in parallel with the water wall tube 4 depending on the initial installed state and hence the surface shape data D obtained by linearly irradiating laser light in the radial direction (X-axis direction) of the water wall tube 4 (see FIG. 4) is θ' degrees off in the lateral direction, the boundary positions between the weld metal and the membranes (or the boundary positions between the tube and the welded portions) are detected manually or automatically, deviation x between the first data and the last data of the surface shape data D is calculated, and a correction is made to move the acquired data by x in the lateral direction in order to match it to an ideal circle. Note that $x_i$ is calculated as $x_i = n_i \times d \times \tan \theta'$. The term "ideal circle" denotes a cross-sectional shape of the water wall tube 4 based on the design data on the water wall tube 4.

As the measurement result, the surface shape obtained from the laser displacement sensor 12 may be inclined or moved up or down depending on vertical vibration of the laser displacement sensor 12 due to vibration during measurement and further on an inclination in the initial installed state. However, an inclination in the circumferential direction of the water wall tube 4 and a vertical positional relationship can be corrected to match the positions of the membranes 8 or the boundary positions P as the references to the membrane positions in the reference shape without reduction in wall thickness. Therefore, superposition to be described later can be performed accurately, and hence measurement error can be reduced.

Even if the laser displacement sensor 12 does not travel in parallel with the water wall tube 4 due to lateral movement depending on the initial installed state, the lateral positional relationship of the water wall tube 4 can be corrected in the same manner, so that superposition can be performed accurately and hence the measurement error can be reduced. Further, since the measurement error can be reduced even if not being parallel, installation time can be reduced to a large extent.

The above-mentioned correction assumes no bend in the water wall tube 4, but the water wall tube 4 in the actual boiler furnace 1 may be curved due to thermal stress generated during operation. Therefore, description will be made of correction of errors from this curvature with reference to FIG. 13.

Figure 13A:
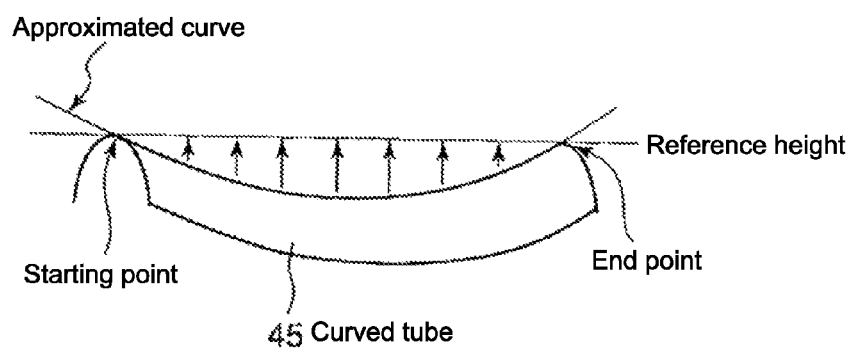
FIG. 13 It is an explanatory drawing showing a correction of a water wall tube in a curved state, where (a) indicates an approximated curve drawn for a curved tube, and (b) indicates data on tube top portions.
Figure 13B:
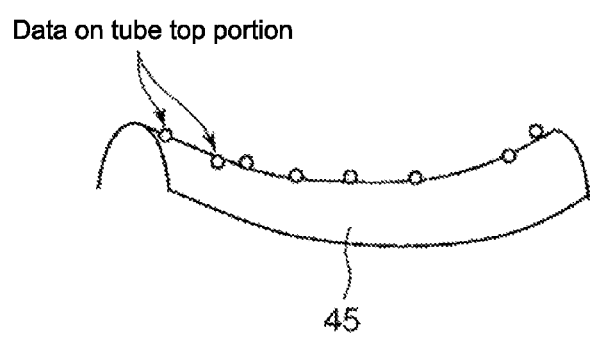

A curved tube 45 as the water wall tube 4 curved as shown in FIG. 13(*a*) has a gap between a curved depressed portion and a reference height that connects a starting point and an endpoint, so that the amount of reduced wall thickness to be evaluated contains a major error. Therefore, a correction is made to raise the curved depressed portion up to the reference height that connects the starting point and the endpoint.

When it is raised up to the reference height by a distance (difference) between the reference height and the top of the curved tube, if the thickness of the apex portion is reduced, the error becomes larger.

Therefore, an approximated curve is required to make the correction to raise the curved depressed portion up to the reference height that connects the starting point and the endpoint. First, as shown in FIG. 13 (b), data on the tube top portion of the curved tube 45 is obtained. The data on the tube top portion can be obtained from the boundary positions between the weld metal and the membranes, more specifically from a midpoint between the boundary positions (3) and (4) between the weld metal and the membranes in FIG. 10(a), from the surface shape data obtained by the laser displacement sensor. Plural data on the tube top portion are acquired from tube cross sections to make an approximation using the least square method. Here, a case where the approximate function is a quadratic function will be described as an example.

The sum $R^2$ of the following quadratic function $$f(x,a)=a_1+a_2+a_3x^2$$

and the square of the distance to each data on the tube top portion is calculated. Here, n=3.

$$R_2=\Sigma[y_i-f(x_i+a_1+a_2+\ldots+a_n)]^2$$

$R^2$ becomes the minimum value in the following condition:

$$\frac{\partial(R^2)}{\partial a_i}=0$$

An approximate expression can be obtained by finding a, which meets the above condition, and an approximated curve as shown in FIG. 13(a) can be drawn. Note that the above technique is just one example of approximation and any other technique such as an order function other than the above.

The difference between the reference height and the approximated curve is so added or subtracted that obtained data will have no curvature. Thus, even when the water wall tube 4 is curved, the correction is made to raise the curved depressed portion up to the reference height, so that the error in evaluating the amount of reduced wall thickness for the curvature of the water wall tube 4 can be reduced.

In the embodiment, since the water wall tube is welded with the membranes, deformation in the lateral direction is small, so that deformation in the axial direction of the water wall tube has only to be considered.

Next, in step S6, the design reference shape of the water wall tube 4 and previous inspection history data are obtained from the plant information database 56, and in step S7, the measurement data on the surface shape corrected in step S4 and step S5 is superposed with the design reference data without reduction in wall thickness, or measurement data in a state without reduction in wall thickness in the previous inspection history, or the ideal circle whose diameter is the distance between (3) and (4).

This superposition is performed based on the surface positions (1), (6) of the membranes 8 or the boundary positions (3), (4) between the weld metal 10 and the water wall tube 4.

Figure 14A:
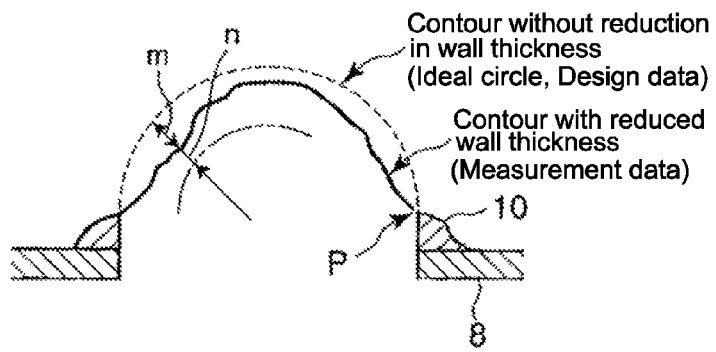
FIGS. 14(a) and 14(b) are explanatory drawings showing calculation of the amount of reduced wall thickness and calculation of remaining tube thickness.
Figure 14B:
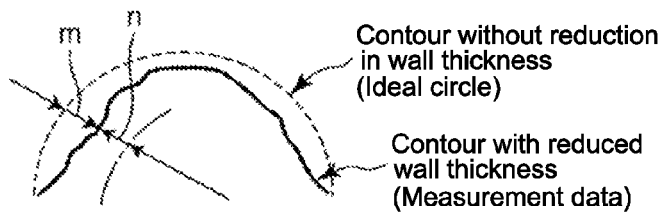
Figure 15:
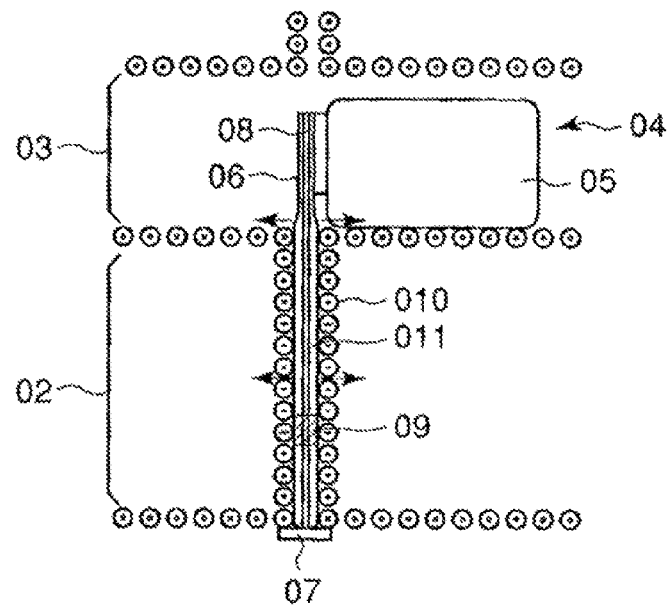
FIG. 15 It is an explanatory drawing showing a conventional technique.

A superposed state in the case of the finned water wall tube 4 is shown in FIG. 14(a), and a superposed state in the case of the water wall tube 4 without membrane is shown in FIG. 14(b).

In the case of the water wall tube 4 without membrane, an ideal circle whose diameter is a distance between the outmost positions is drawn from the measurement data, superimposed and compared.

Since the degree of corrosion in the membrane 8 is lower than the circumferential surface of the water wall tube 4 that faces the inside of the boiler furnace 1, the membrane 8 is suitable for use as a reference position. When the amount of reduced wall thickness of the water wall tube 4 is slight, the error in calculating a difference obtained from the superposition between the measurement result and the reference shape without reduction in wall thickness is small and hence inspection error is small. However, as the amount of reduced wall thickness increases, the thickness of the membrane 8 is reduced. Therefore, when the amount of reduced wall thickness becomes large, the thickness of the membrane 8 needs to be measured by an ultrasonic thickness measuring unit to correct the surface position of the membrane 8 as well.

Further, one tube top portion may be measured by the ultrasonic thickness measuring unit so that the value can be used as a correction value in the up-down direction after calculation of the amount of reduced wall thickness.

When the water wall tubes 4 are separate tubes without being connected by the membranes 8, both end portions of the surface shape from the measurement data, i.e., positions of contact with adjacent water wall tubes 4 or the closest positions are used as reference positions as shown in FIG. 14(b). This is because not only such positions are less likely to be exposed to the combustion gas and hence the degree of corrosion is low, but also the ideal circle whose diameter is the distance between both ends of the surface shape can be drawn and this makes it easy to calculate the amount of reduced wall thickness.

Next, the procedure exceeds to step S8 in which the surface shape from the measurement data and the data without reduction in wall thickness, both superposed in S7, are compared to calculate distance m (see FIG. 14(a)) obtained by subtracting a contour shape of the measurement data from the distance (radius) from the circle center of the data without reduction in wall thickness to a contour position. Then, in step S9, this distance m is determined to be the amount, m, of reduced wall thickness.

Next, the procedure proceeds to step S10 to compare the amount m with a reduced wall thickness reference value and output the result in step S11.

This reduced wall thickness reference value is set (T1-T2) based on the design wall thickness (thickness T1 without reduction in wall thickness) of the water wall tube 4 and the design requiring thickness (thickness T2 required in design), both stored in the plant information database 56. If it reaches the reduced wall thickness reference value, the measured portion is color-coded, such as red-coded, when the display section 54 displays the measurement result on the screen to alert a worker and a plant manager.

Next, in step S12, the design requiring thickness (thickness T2 required in design) of the water wall tube 4 and information on the design wall thickness (thickness T1 without reduction in wall thickness), both stored in the plant information database 56, are obtained, and in step S13, remaining tube wall thickness n is calculated by subtracting the amount, m, of reduced wall thickness calculated in step S9 from the design wall thickness (thickness T1 without reduction in wall thickness).

Then, in step S14, the remaining tube wall thickness n is compared with the design requiring thickness (thickness T2 required in design) as a reference, the remaining thickness state is output in step S15, and the procedure proceeds to step S16 to end.

Like in step S11, if the output in step S15 reaches the design requiring thickness, the measured portion is color-coded, such as red-coded, when the display section 54 displays the measurement result on the screen.

The remaining tube wall thickness n is determined by subtracting the amount, m, of reduced wall thickness from the design wall thickness T1 to evaluate the corrosion condition from whether the remaining tube wall thickness n meets the design requiring thickness T2, and this enables reliable, efficient maintenance and inspection.

Since the actual water wall tube 4 is manufactured with an excess pad of 2-3 percent on the internal diameter side more than the design wall thickness in consideration of manufacturing error, a critical corrosion condition can be determined, leaving a margin for error.

INDUSTRIAL APPLICABILITY

According to the present invention, since the reduced wall thickness state of multiple water wall tubes extending in the up-down direction (vertical direction) along the inner wall surfaces of the boiler furnace can be inspected over a wide range accurately and efficiently based on the surface shapes of the water wall tubes measured by the laser displacement sensor, this is useful to be applied to an inspection device for boiler furnace water wall tubes.

The invention claimed is:

1. An inspection device for boiler furnace water wall tubes, which inspects reduced wall conditions of multiple water wall tubes extending in a vertical direction along inner wall surfaces of a boiler furnace and arranged adjacent to each other, comprising:
    a leg placed upright and fixed by a magnet onto a surface of a water wall tube;
    a support frame fixed to the leg to support a displacement sensor producing laser light to be irradiated onto the surface of the water wall tube;
    a moving mechanism for moving the displacement sensor in an axial direction of the water wall tube relative to the support frame; and
    a signal processing unit configured to calculate an amount of reduced wall thickness of the water wall tube from a difference between data of a surface shape of the water wall tube along a direction substantially perpendicular to the axial direction of the water wall tube obtained by the displacement sensor and data of a reference shape without reduction in wall thickness in order to evaluate a reduced wall thickness condition, the signal processing unit including a reference position calculating section for calculating a reference position for superposition between the data of the surface shape and data of the reference shape.

2. The inspection device for boiler furnace water wall tubes according to claim 1, wherein the support frame is supported by a plurality of the legs and the inspection device further comprising:
    adjustment mechanisms configured to move the displacement sensor in the upright direction of the legs and in a direction perpendicular to the upright direction and the axial direction of the water wall tube to make a position of the displacement sensor adjustable relative to the water wall tube.

3. The inspection device for boiler furnace water wall tubes according to claim 1, wherein the signal processing unit includes a correction section for correcting an inclination and position of the surface shape based on the signal from the displacement sensor at the time of the superposition.

4. The inspection device for boiler furnace water wall tubes according to claim 1, wherein the reference position is a position of a membrane provided to protrude radially in order to connect adjacent water wall tubes.

5. The inspection device for boiler furnace water wall tubes according to claim 1, wherein the reference position is a contact or closest position between adjacent water wall tubes.

6. The inspection device for boiler furnace water wall tubes according to claim 1, further comprising refraction means provided between the displacement sensor producing laser light to be irradiated onto the surface of the water wall tube and the water wall tube to refract the laser light irradiated from the displacement sensor toward the water wall tube.

7. An inspection method for boiler furnace water wall tubes, which inspects reduced wall conditions of water wall tubes extending in a vertical direction along inner wall surfaces of a boiler furnace and arranged adjacent to each other, comprising:
    measuring a surface shape of a water wall tube along a direction substantially perpendicular to an axial direction of the water wall tube based on a signal from a displacement sensor for irradiating laser light onto the surface of the water wall tube;
    superposing a measurement result of the surface shape and a reference shape without reduction in wall thickness to calculate a difference therebetween based on a reference position of the surface shape; and
    calculating an amount of reduced wall thickness of the water wall tube from the difference to evaluate a reduced wall condition.

8. The inspection method for boiler furnace water wall tubes according to claim 7, wherein an inclination and a position of the surface shape based on the signal from the displacement sensor are corrected and superposed at the time of the superposition.

9. The inspection method for boiler furnace water wall tubes according to claim 8, wherein a remaining tube wall thickness is determined by subtracting the calculated amount of reduced wall thickness from a design wall thickness, and the remaining tube wall thickness is evaluated depending on whether the remaining tube wall thickness meets a design requiring wall thickness.

* * * * *